United States Patent [19]

Law et al.

[11] Patent Number: 4,644,082

[45] Date of Patent: Feb. 17, 1987

[54] PHOTOCONDUCTIVE DEVICES CONTAINING NOVEL BENZYL FLUORINATED SQUARAINE COMPOSITIONS

[75] Inventors: Kock-Yee Law, Fairport; Frank C. Bailey, Webster, both of N.Y.

[73] Assignee: Xerox Corporation, Stamford, Conn.

[21] Appl. No.: 682,716

[22] Filed: Dec. 17, 1984

Related U.S. Application Data

[62] Division of Ser. No. 558,248, Dec. 5, 1983, Pat. No. 4,508,803.

[51] Int. Cl.[4] ........................ C07C 87/50; C07C 87/52

[52] U.S. Cl. .................................................... 564/307

[58] Field of Search ........................................ 564/307

[56] References Cited

U.S. PATENT DOCUMENTS

| | | | |
|---|---|---|---|
| 4,471,041 | 9/1984 | Baranyi et al. | 564/307 UX |
| 4,481,270 | 11/1984 | Kubota et al. | 564/307 UX |
| 4,486,520 | 12/1984 | Yanus | 564/307 UX |
| 4,489,148 | 12/1984 | Horgan | 564/307 UX |
| 4,500,621 | 2/1985 | Wurster | 564/307 UX |

*Primary Examiner*—Paul F. Shaver

*Attorney, Agent, or Firm*—E. O. Palazzo

[57] ABSTRACT

Disclosed are the use of novel squaraine compositions selected from the group consisting of bis(2-fluoro-4-methylbenzylaminophenyl)squaraine, bis(2-fluoro-4-methyl-p-chlorobenzylaminophenyl)squaraine, bis(2-fluoro-4-methyl-p-fluorobenzylaminophenyl)squaraine, and bis(2-fluoro-4-methyl-m-chlorobenzylaminophenyl)squaraine, in photoresponsive devices, particularly layered photoresponsive devices which are sensitive to infrared and/or visible illumination.

5 Claims, 5 Drawing Figures

PHOTOCONDUCTIVE DEVICES CONTAINING NOVEL BENZYL FLUORINATED SQUARAINE COMPOSITIONS

This is a division of application Ser. No. 558,248, filed Dec. 5, 1983, now U.S. Pat. No. 4,508,803.

BACKGROUND

This invention is generally directed to novel squaraine compositions of matter, and the incorporation of these compositions into layered photoresponsive devices. In one embodiment of the present invention there are provided novel fluoro benzylamino squaraine compositions of matter, useful as organic photoconductive materials in layered photoresponsive devices, especially those devices containing amine hole transport layers. There is thus provided in accordance with the present invention a photoresponsive device containing as a photoconductive layer novel fluoro benzylamino squaraine compositions of matter. The sensitivity of these photoresponsive devices can be varied or enhanced, enabling them to be responsive to visible light, and infrared illumination needed for laser printing. Accordingly a photoresponsive device containing the fluoro benzylamino squaraines of the present invention can function so as to enhance or reduce the intrinsic properties of a charge carrier photogenerating material contained therein, in the infra-red and/or visible range of the spectrum thereby allowing the device to be sensitive to either visible light and/or infrared wavelengths.

Numerous different xerographic photoconductive members are known including, for example, a homogeneous layer of a single material such as vitreous selenium, or a composite layered device, containing a dispersion of a photoconductive composition. An example of one type of composite xerographic photoconductive member is described for example, in U.S. Pat. No. 3,121,006, wherein there is disclosed finely divided particles of a photoconductive inorganic compound dispersed in an electrically insulating organic resin binder. These members contain for example coated on a paper backing a binder layer containing particles of zinc oxide uniformly dispersed therein. The binder materials disclosed in this patent comprise a material such as polycarbonate resins, polyester resins, polyamide resins, and the like which are incapable of transporting for any significant distance injected charge carriers generated by the photoconductive particles. Accordingly, as a result the photoconductive particles must be in a substantially contiguous particle to particle contact throughout the layer for the purpose of permitting charge dissipation required for a cyclic operation. Thus, with the uniform dispersion of photoconductive particles described a relatively high volume concentration of photoconductor material, about 50 percent by volume, is usually necessary in order to obtain sufficient photoconductor particle to particle contact for rapid discharge. This high photoconductive loading can result in destroying the physical continuity of the resinous binder, thus significantly reducing the mechanical properties thereof.

There are also known photoreceptor materials comprised of inorganic or organic materials wherein the charge carrier generating, and charge carrier transport functions are accomplished by discrete contiguous layers. Additionally, layered photoreceptor materials are disclosed in the prior art which include an overcoating layer of an electrically insulating polymeric material. However, the art of xerography continues to advance and more stringent demands need to be met by the copying apparatus in order to increase performance standards, and to obtain higher quality images. Also, there is desired layered photoresponsive devices which are responsive to visible light, and/or infrared illumination selected for laser printing systems.

Recently, there has been disclosed other layered photoresponsive devices including those comprised of separate generating layers, and transport layers as described in U.S. Pat. No. 4,265,990, and overcoated photoresponsive materials containing a hole injecting layer, overcoated with a hole transport layer, followed by an overcoating of a photogenerating layer, and a top coating of an insulating organic resin, reference U.S. Pat. No. 4,251,612. Examples of photogenerating layers disclosed in these patents include trigonal selenium, and phthalocyanines, while examples of transport layers include certain diamines as mentioned herein. The disclosures of each of these patents, namely, U.S. Pat. Nos. 4,265,990 and 4,251,612 are totally incorporated herein by reference.

Many other patents are in existence describing photoresponsive devices including layered devices containing generating substances, such as U.S. Pat. No. 3,041,167, which discloses an overcoated imaging member containing a conductive substrate, a photoconductive layer, and an overcoating layer of an electrically insulating polymeric material. This member is utilized in an electrophotographic copying system by, for example, initially charging the member, with an electrostatic charge of a first polarity, and imagewise exposing to form an electrostatic latent image which can be subsequently developed to form a visible image. Prior to each succeeding imaging cycle, the imaging member can be charged with an electrostatic charge of a second polarity, which is opposite in polarity to the first polarity. Sufficient additional charges of the second polarity are applied so as to create across the member a net electrical field of the second polarity. Simultaneously, mobile charges of the first polarity are created in the photoconductive layer such as by applying an electrical potential to the conductive substrate. The imaging potential which is developed to form the visible image, is present across the photoconductive layer and the overcoating layer.

There is also disclosed in Belgium Pat. No. 763,540, an electrophotographic member having at least two electrically operative layers. The first photoconductive layer is capable of photogenerating charge carriers, and injecting the carriers into a continuous active layer containing an organic transporting material which is substantially non-absorbing in the spectral region of intended use, but which is active in that it allows the injection of photogenerated holes from the photoconductive layer and allows these holes to be transported through the active layer. Additionally, there is disclosed in U.S. Pat. No. 3,041,116, a photoconductive material containing a transparent plastic material overcoated on a layer of vitreous selenium contained on a substrate.

Furthermore, there is disclosed in U.S. Pat. Nos. 4,232,102 and 4,233,383, photoresponsive imaging members comprised of trigonal selenium doped with sodium carbonate, sodium selenite, and trigonal selenium doped with barium carbonate, and barium selenite or mixtures thereof. Moreover, there is disclosed in U.S. Pat. No.

3,824,099, certain photosensitive hydroxy squaraine compositions. According to the disclosure of this patent the squaraine compositions are photosensitive in normal electrostatographic imaging systems.

Also there is disclosed in a copending application the use of known squaraine compositions, such as hydroxy squaraines, as a photoconductive layer in an infrared sensitive photoresponsive device. More specifically there is described in the copending application an improved photoresponsive device containing a substrate, a hole blocking layer, an optional adhesive interfacial layer, an inorganic photogenerating layer, a photoconductive composition capable of enhancing or reducing the intrinsic properties of the photogenerating layer, which photoconductive composition is selected from various squaraine compositions, including hydroxy squaraine compositions, and a hole transport layer.

Addtionally there is disclosed in a copending application the use of novel julolidinyl squaraine compositions, such as bis-9-(8-hydroxyjulolidinyl)squaraine, as photoconductive substances in photoresponsive devices which are sensitive either to infrared light, and/or visible illumination. As indicated in this copending application the improved photoresponsive device in one embodiment is comprised of a supporting substrate, a hole blocking layer, an optional adhesive interfacial layer, an inorganic photogenerating layer, a photoconducting composition capable of enhancing or reducing the intrinsic properties of the photogenerating layer, which composition is comprised of the novel julolidinyl squaraine compositions disclosed therein, and a hole transport layer. The disclosure of the referenced copending application U.S. Ser. No. 493,114, filed 5/9/83, now U.S. Pat. No. 4,471,041 entitled Photoconductive Devices Containing Novel Squaraine Compositions, is totally incorporated herein by reference.

While squaraine compositions are known, there continues to be a need for novel squaraine compositions, particularly squaraine compositions of superior photosensitivity. Addtionally there continues to be a need for photoresponsive devices containing as a photoconductive layer novel squaraine compositions of matter which are highly photosensitive. Additionally there continues to be a need for novel squaraine materials which when selected for layered photoresponsive imaging devices allow the generation of acceptable images, and wherein such devices can be repeatedly used in a number of imaging cycles without deterioration thereof from the machine environment or surrounding conditions. Moreover, there continues to be a need for improved layered imaging members wherein the squaraine materials selected for one of the layers are substantially inert to users of such devices. Furthermore, there continues to be a need for overcoated photoresponsive devices which are sensitive to a broad range of wavelengths, and more specifically are sensitive to infrared light, and visible light, thereby allowing such devices to be used in a number of imaging and printing systems.

SUMMARY OF THE INVENTION

It is therefore an object of the present invention to provide novel fluoro benzylamino squaraine compositions of matter.

In another object of the present invention there are provided improved photoresponsive imaging members containing novel fluoro benzylamino squaraine compositions.

It is yet another object of the present invention to provide improved photoresponsive devices which are panchromatic, and thus sensitive to visible light as well as infrared light.

A further specific object of the present invention is the provision of an improved overcoated photoresponsive device containing a photoconductive layer comprised of novel squaraine photosensitive pigments, and a hole transport layer.

It is yet another object of the present invention to provide an improved overcoated photoresponsive device containing a hole transport layer and coated thereover a photoconductive layer containing novel fluoro benzylamino squaraine compositions.

In yet another object of the present invention there is provided a photoresponsive device containing a photoconductive composition comprised of novel fluoro benzylamino squaraine compositions situated between a hole transport layer, and a photogenerating layer.

It is yet another object of the present invention to provide an improved layered overcoated photoresponsive device containing a novel squaraine photoconductive composition situated between a photogenerating layer, and the supporting substrate of such a device.

Another object of the present invention resides in the provision of an improved overcoated photoresponsive device containing a photogenerating composition situated between a hole transport layer and a photoconductive layer comprised of novel fluoro benzylamino squaraine compositions, which device is simultaneously responsive to infrared light and visible light.

In another object of the present invention there is provided an improved overcoated photoresponsive device containing a photoconductive layer comprised of the novel squaraine compositions described herein, situated between a hole transport layer, and a layer comprised of a photogenerating composition, which device is simultaneously responsive to infrared light and visible light.

In yet another object of the present invention there are provided imaging and printing methods with the improved overcoated photoresponsive devices described herein.

These and other objects of the present invention are accomplished by providing novel fluoro benzyl squaraine compositions of matter selected from the group consisting of (I) bis(2-fluoro-4-methyl benzylaminophenyl)squaraine, (II) bis(2-fluoro-4-methyl-parachlorobenzylaminophenyl)squaraine, (III) bis(2-fluoro-4-methyl-parafluorobenzylaminophenyl)squaraine, and (IV) bis(2-fluoro-4-methyl-m-chlorobenzylaminophenyl)squaraine. These squaraine compositions are of the following formulas:

I.

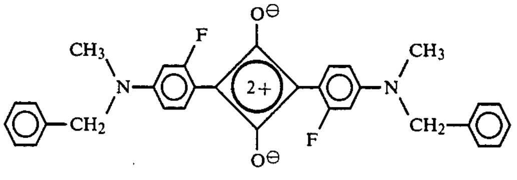

-continued

II.

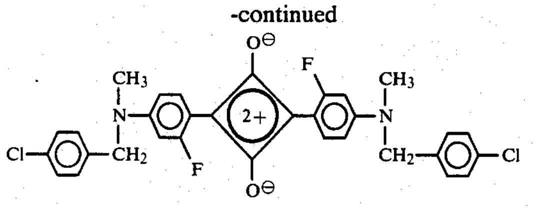

III.

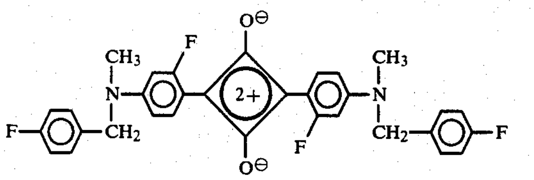

IV.

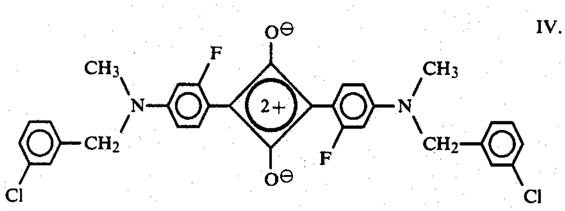

The novel squaraine compositions disclosed herein are generally prepared by the reaction of appropriate fluoro aniline derivatives, such as meta-fluoro-N-methyl-N-benzylaniline, and squaric acid, in a molar ratio of from about 4 to about 1, and preferably in a ratio of from about 1.5 to 2.5, in the presence of an aliphatic alcohol, and an optional azeotropic cosolvent. About 400 milliliters of alcohol per 0.1 moles of squaric acid are used, however up to 1,000 milliliters of alcohol to 0.1 moles of squaric acid can be selected. The reaction is generally accomplished at a temperature of from about 75 degrees Centigrade to about 130 degrees Centigrade, and preferably at a temperature of 95 degrees Centigrade to 105 degrees Centigrade, with stirring, until the reaction is completed. Subsequently the desired product is isolated from the reaction mixture by known techniques such as filtration, and the product identified by analytical tools including NMR, and mass spectroscopy. Further carbon, hydrogen, fluorine, nitrogen, and oxygen elemental analysis is selected for aiding in identifying the resultant product.

The fluoroaniline derivatives can be prepared by a number of processes thus, for example, known fluoroanilines, such as metafluoroaniline are reacted with trialkyl orthoformates, including trimethyl orthoformate in a molar ratio of from about 1 to about 1.5, thereby resulting in N-alkyl-meta-fluoroformanilide, such as N-methyl-metafluoroformanilide. Generally this reaction is accomplished by mixing the reactants and heating to a high temperature, over about 200° C. followed by distillation. Thereafter, the resulting anilide product is hydrolyzed with an acid, such as hydrochloric acid, causing the formation of N-alkyl-meta-fluoroaniline, and specifically, for example, N-methyl-meta-fluoroaniline. Subsequently, a benzyl halide derivative, including benzyl chloride, is reacted with the formed aniline product, in a molar ratio of from about 1:1, by mixing these reactants and heating to a temperature so as to cause the reaction to proceed, usually above 100°-110° C. This results in the aniline derivative reactant such as N-alkyl-N-benzyl-meta-fluoroaniline, and preferably N-methyl-N-benzyl-meta-fluoroaniline, which is then reacted with the squaric acid as described herein enabling the formation of the novel fluoro squaraines of the present invention, reference formulas I-IV.

Illustrative examples of fluoro aniline derivative reactants selected for preparing the novel squaraines of the present invention include meta-fluoro-N-methyl-N-benzylaniline, meta-fluoro-N-methyl-N-parafluoro-benzylaniline, meta-fluoro-N-methyl-N-para-chlorobenzylaniline, and meta-fluoro-N-methyl-meta-chlorobenzylaniline. When the meta-fluoro-N-methyl-N-benzylaniline is selected as one of the reactants, there results the bis(2-fluoro-4-methylbenzylaminophenyl)-squaraine represented by formula I. Similarly, when there is selected as the reactants the meta-fluoro-N-methyl-N-para-chlorobenzylaniline, meta-fluoro-N-methyl-N-parafluorobenzylaniline, or meta-fluoro-N-methyl-N-metachlorobenzylaniline, there results the squaraines of the formula as represented by II, III and IV, respectively, disclosed hereinbefore.

Illustrative examples of aliphatic alcohols selected for preparing the fluoro benzyl squaraines of the present invention include 1-butanol, 1-pentanol, hexanol, and heptanol, while illustrative examples of azeotropic materials selected include aromatic compositions such as benzene, toluene, and xylene.

The improved layered photoresponsive devices of the present invention are comprised in one embodiment of a supporting substrate, a hole transport layer, and as a photoconductive layer situated between the supporting substrate, and the hole transport layer the novel fluorinated squaraine compositions of the present invention. In another embodiment there is envisioned a layered photoresponsive device comprised of a supporting substrate, a photoconductive layer comprised of the novel fluorinated squaraine compositions of the present invention and situated between the supporting substrate, and the photoconductive layer, a hole transport layer. Also provided in accordance with the present invention are improved photoresponsive devices useful in printing systems comprising a layer of a photoconductive composition situated between a photogenerating layer, and a hole transport layer, or wherein the photoconductive composition is situated between a photogenerating layer and the supporting substrate of such a device, the photoconductive composition being comprised of the novel fluorinated squaraine compositions of the present invention. In the latter devices, for example, the photoconductive layer serves to enhance, or reduce the intrinsic properties of the photogenerating layer in the infrared and/or visible range of the spectrum.

In one specific illustrative embodiment, the improved photoresponsive device of the present invention is comprised in the order stated of (1) a supporting substrate, (2) a hole blocking layer, (3) an optional adhesive interface layer, (4) an inorganic photogenerator layer, (5) a photoconducting composition layer comprised of the novel squaraine materials described herein, and (6) a hole transport layer. Thus the photoresponsive device of the present invention in one important embodiment is comprised of a conductive supporting substrate, a hole blocking metal oxide layer in contact therewith, an adhesive layer, an inorganic photogenerating material overcoated on the adhesive layer, a photoconducting fluoro squaraine composition of the formulas I-IV, which for example is capable of enhancing or reducing the intrinsic properties of the photogenerating layer in the infrared and/or visible range of the spectrum, and as a top layer, a hole transport layer comprised of certain diamines dispersed in a resinous matrix. The photoconductive layer composition when in contact with the hole transport layer is capable of allowing holes generated by the photogenerating layer to be transported. Further the photoconductive layer does not substantially trap holes generated in the photogenerating layer, and also the photoconductive squaraine composition layer can function as a selective filter, allowing light of a certain wavelength to penetrate the photogenerating layer.

In another important embodiment, the present invention is directed to an improved photoresponsive device as described hereinbefore, with the exception that the photoconductive fluoro squaraine composition is situated between the photogenerating layer and the supporting substrate contained in the device. Accordingly, in this variation, the photoresponsive device of the present invention is comprised in the order stated of (1) a substrate, (2) a hole blocking layer, (3) an optional adhesive or adhesion interface layer, (4) a photoconductive composition comprised of the novel squaraine materials disclosed herein, (5) an inorganic photogenerating layer, and (6) a hole transport layer.

Exposure to illumination and erasure of the layered photoresponsive devices of the present invention may be accomplished from the front side, the rear side or combinations thereof.

The improved photoresponsive devices of the present invention can be prepared by a number of known methods, the process parameters and the order of coating of the layers being dependent on the device desired. Thus, for example, a three layered photoresponsive device can be prepared by vacuum sublimation of the photoconducting layer on a supporting substrate, and subsequently depositing by solution coating the hole transport layer. In another process variant, the layered photoresponsive device can be prepared by providing the conductive substrate containing a hole blocking layer and an optional adhesive layer, and applying thereto by solvent coating processes, laminating processes, or other methods, a photogenerating layer, a photoconductive composition comprised of the novel squaraines of the present invention, which squaraines are capable of enhancing or reducing the intrinsic properties of the photogenerating layer in the infrared and/or visible range of the spectrum, and a hole transport layer.

In one specific preparation sequence, there is provided a 20 percent transmissive aluminized Mylar substrate, of a thickness of about 3 mils, which is coated with a one-half mil Bird applicator, at about room temperature with an adhesive, such as the adhesive available from E. I. duPont as 49,000, contained in a methylene chloride/trichloroethane solvent, followed by drying at 100 degrees Centigrade. Subsequently, there is applied to the adhesive layer a photoconductive layer comprised of the fluorinated squaraines of the present invention, which application is also accomplished with a Bird applicator, with annealing at 135 degrees Centigrade, followed by a coating of the amine transport layer. The amine transport layer is applied by known solution coating techniques, with a 5 mil Bird applicator and annealing at 135 degrees Centigrade, wherein the solution contains about 20 to about 80 percent by weight of the amine transport molecule, and from about 80 to about 20 weight percent of a resinous binder substance, such as a polycarbonate material.

The improved photoresponsive devices of the present invention can be incorporated into various imaging systems, such as those conventionally known as xerographic imaging processes. Additionally, the improved photoresponsive devices of the present invention containing an inorganic photogenerating layer, and a photoconductive layer comprised of the novel squaraines of the present invention can function simultaneously in imaging and printing systems with visible light and/or infrared light. In this embodiment, the improved photoresponsive devices of the present invention may be negatively charged, exposed to light in a wavelength of from about 400 to about 1,000 nanometers, either sequentially or simultaneously, followed by developing the resulting image and transferring to paper. The above sequence may be repeated many times.

BRIEF DESCRIPTION OF THE DRAWINGS

For a better understanding of the present invention and further features thereof reference is made to the following detailed description of various preferred embodiments wherein.

DESCRIPTION OF THE PREFERRED EMBODIMENTS

The preferred embodiments will now be illustrated with reference to specific photoresponsive devices containing the novel fluoro benzyl squaraine compositions illustrated herein, it being noted that equivalent compositions are also embraced with the scope of the present invention.

Figure 1:
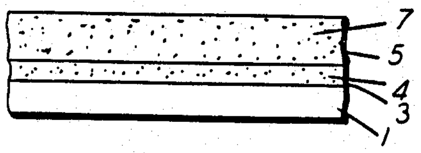
FIGS. 1 to 5 are partially schematic cross-sectional views of the photoresponsive devices of the present invention.

Illustrated in FIG. 1 is the photoresponsive device of the present invention comprised of a substrate 1, a photoconductive layer 3, comprised of the novel squaraine composition bis(2-fluoro-4-methylbenzylaminophenyl)-squaraine, optionally dispersed in a resinous binder composition 4, and a charge carrier hole transport layer 5, dispersed in an inactive resinous binder composition 7.

Figure 2:
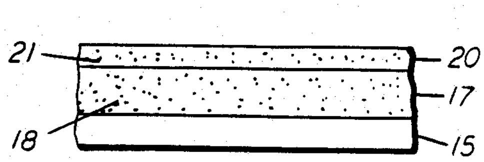

Illustrative in FIG. 2 is essentially the same device as shown in FIG. 1, with the exception that the hole transport layer is situated between the supporting substrate and the photoconductive layer. More specifically with reference to this Figure, there is illustrated a photoresponsive device comprised of a supporting substrate 15, a hole transport layer 17, comprised of a hole transport composition dispersed in an inert resinous binder composition 18, and a photoconductive layer 20 comprised of the squaraine composition bis(2-fluoro-4-methylbenzylaminophenyl)squaraine of the present invention, optionally dispersed in a resinous binder composition 21.

Figure 3:
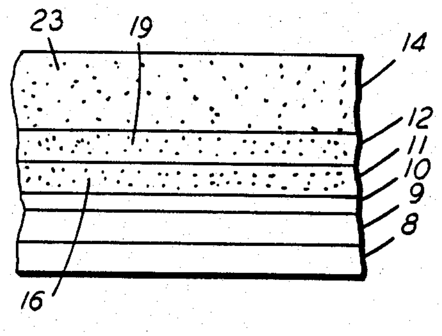

Illustrated in FIG. 3 is a photoresponsive device of the present invention, comprised of a substrate 8, a hole blocking metal oxide layer 9, an optional adhesive layer 10, a charge carrier inorganic photogenerating layer 11, an organic photoconductive composition layer 12 comprised of bis(2-fluoro-4-methylbenzylaminophenyl)-squaraine, which composition enhances or reduces the intrinsic properties of the photogenerator layer 11 in the infrared and/or visible range of the spectrum, and a charge carrier or hole transport layer 14. The photogenerator layer 11 is generally comprised of a photogenerating substance optionally dispersed in a resinous binder composition 16, and similarly, the organic photoconductive layer 12 contains the fluoro squaraine material optionally dispersed in the resinous binder 19. The charge transport layer 14 contains a charge transporting substance, such as an amine composition, optionally dispersed in an inactive resinous binder material 23.

Figure 4:
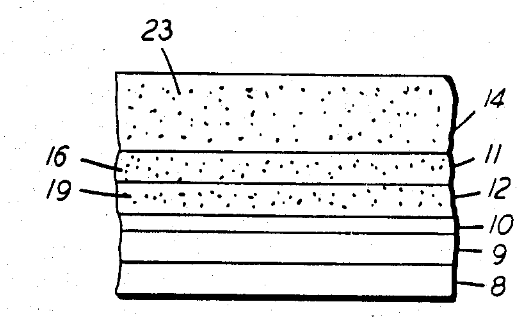

Illustrated in FIG. 4 is essentially the same device as illustrated in FIG. 3 with the exception that the photoconductive layer 12 is situated between the inorganic photogenerating layer 11 and the substrate 8, and more specifically, the photoconductive layer 12 in this embodiment is specifically situated between the optional adhesive layer 10 and the inorganic photogenerating layer 11.

Figure 5:
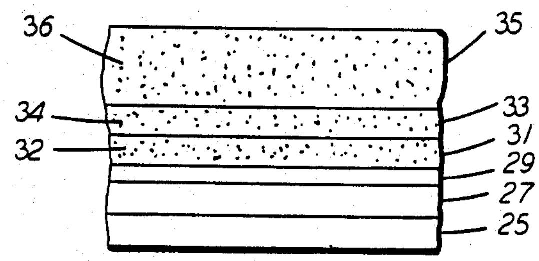

Illustrated in FIG. 5 is a further photoresponsive device of the present invention, wherein the substrate 25 is comprised of Mylar in a thickness of 3 mils, containing a layer of 20 percent transmissive aluminum in a thickness of about 100 Angstroms, a metal oxide layer 27 comprised of aluminum oxide in a thickness of about 20 Angstroms, a polyester adhesive layer 29, which polyester is commercially available from E. I. duPont as 49,000 polyester, this layer being of a thickness of 0.5 microns, an inorganic photogenerating layer 31; of a thickness of about 2.0 microns, and comprised of 10 weight percent of $Na_2SeO_3$ and $Na_2CO_3$ doped trigonal selenium, in a polyvinylcarbazole binder 32, 90 weight percent, a photoconductive layer 33, in a thickness of about 0.5 microns, and comprised of 30 weight percent of bis(2-fluoro-4-methylbenzylaminophenyl)squaraine, dispersed in the resinous binder 34, PE-200, a polyester, commercially availble from Goodyear Chemical, 70 weight percent and a hole transport layer 25, in a thickness of about 25 microns, comprised of 50 weight percent of N,N'-diphenyl-N,N'-bis(3-methylphenyl)-[1,1'-biphenyl]-4,4'-diamine, dispersed in a polycarbonate resinous binder 36.

With reference to FIGS. 1 to 5, the photoconductive layer can be comprised of the other squaraine compositions illustrated herein, reference the squaraine compositions as specified with regard to formulas II–IV.

With further reference to the Figures, the substrates may comprise a layer of insulating material such as an inorganic or organic polymeric material, including Mylar a commercially available polymer; a layer of an organic or inorgaic material having a semi-conductive surface layer such as indium tin oxide, or aluminum arranged thereon, or a conductive material such as, for example, aluminum, chromium, nickel, brass or the like. The substrate may be flexible or rigid and many have a number of many different configurations, such as, for example, a plate, a cylindrical drum, a scroll, an endless flexible belt and the like. Preferably, the substrate is in the form of an endless flexible belt. In some situations, it may be desirable to coat on the back of the substrate, particularly when the substrate is an organic polymeric material, an anti-curl layer, such as for example, polycarbonate materials commercially available as Makrolon.

The thickness of the substrate layer depends on many factors, including economical considerations, thus this layer may be of substantial thickness, for example, over 100 mils, or of minimum thickness, providing there are no adverse effects on the system. In one preferred embodiment the thickness of this layer is from about 3 mils to about 10 mils.

The hole blocking metal oxide layers can be comprised of various suitable known materials including aluminum oxide, and the like. The primary purpose of this layer is to provide hole blocking, that is to prevent hole injection from the substrate during and after charging. Typically, this layer is of a thickness of less than 50 Angstroms.

The adhesive layers are typically comprised of a polymeric material, including polyesters, polyvinyl butyral, polyvinyl pyrrolidone and the like. Typically, this layer is of a thickness of less than about 0.6 microns.

The inorganic photogenerating layer can be comprised of known photoconductive charge carrier generating materials sensitive to visible light, such as amorphous selenium, amorphous selenium alloys, halogen doped amorphous selenium, halogen doped amorphous selenium alloys, trigonal selenium, mixtures of Groups IA and IIA elements, selenite and carbonates with trigonal selenium, reference U.S. Pat. Nos. 4,232,102 and 4,233,283, the disclosure of each of these patents being totally incorporated herein by reference, cadmium sulfide, cadmiun selenide, cadmium telluride, cadmium sulfur selenide, cadmiun sulfur telluride, cadmium seleno telluride, copper, and chlorine doped cadmium sulfide, cadmium selenide and cadmium sulfur selenide and the like. Alloys of selenium included within the scope of the present invention include selenium tellurium alloys, selenium arsenic alloys, selenium tellurium arsenic alloys, and preferably such alloys containing a halogen material such as chlorine in an amount of from about 50 to about 200 parts per million.

The photogenerating layer can also contain organic materials including for example, metal phthalocyanines, metal-free phthalocyanines, vanadyl phthalocyanine, and the like. Examples of phthalocyanine substances are disclosed in U.S. Pat. No. 4,265,990, the disclosure of which is totally incorporated herein by reference. Preferred organic substances for the photogenerating layer include vanadyl phthalocyanine and x-metal-free phthalocyanine.

This layer typically has a thickness of from about 0.05 microns to about 10 microns or more, and preferably is of a thickness from about 0.4 microns to about 3 microns, however, the thickness of this layer is primarily dependent on the photoconductive weight loading, which may vary from 5 to 100 weight percent. Generally, it is desirable to provide this layer in a thickness which is sufficient to absorb about 90 percent or more of the incident radiation which is directed upon it in the imagewise or printing exposure step. The maximum thickness of this layer is dependent primarily upon factors such as mechanical considerations, for example whether a flexible photoresponsive device is desired.

A very important layer of the photoresponsive device of the present invention is the photoconductive layer comprised of the novel squaraine compositions disclosed herein, reference formulas I, II, III and IV. These compositions, which are generally electronically compatible with the charge carrier transport layer, enable photoexcited charge carriers to be injected into the transport layer, and further allow charge carriers to travel in both directions across the interface between the photoconductive layer and the charge transport layer.

Generally, the thickness of the photoconductive layer depends on a number of factors including the thicknesses of the other layers, and the percent mixture of photoconductive material contained in this layer. Accordingly, this layer can range in thickness of from about 0.05 microns to about 10 microns when the photoconductive squaraine composition is present in an amount of from about 5 percent to about 100 percent by weight, and preferably this layer ranges in thickness of from about 0.25 microns to about 1 micron, when the photoconductive squaraine composition is present in this layer in an amount of 30 percent by weight. The maximum thickness of this layer is dependent primarily upon factors such as mechanical considerations, for example whether a flexible photoresponsive device is desired.

The inorganic photogenerating materials or the photoconductive materials can comprise 100 percent of the respective layers, or these materials can be dispersed in various suitable inorganic or resinous polymer binder materials, in amounts of from about 5 percent by weight to about 95 percent by weight, and preferably in amounts of from about 25 percent by weight to about 75 percent by weight. Illustrative examples of polymeric binder resinous materials that can be selected for the photogenerating composition include those as disclosed, for example, in U.S. Pat. No. 3,121,006, the disclosure of which is totally incorporated herein by reference, polyesters, polyvinyl butyral, Formvar®, polycarbonate resins, polyvinyl carbazole, epoxy resins, phenoxy resins, especially the commercially available poly(hydroxyether) resins, and the like. Resinous binders for the fluoro squaraine photoconductive compositions can be selected from similar binder materials as described herein with reference to the photogenerating binder, however, the resinous binders for the photoconductive material is generally selected from polycarbonates, such as those commercially available as Makrolon, polyesters including those commercially available from Goodyear Chemical as PE-200, polyvinylformal, and polyvinylbutyral.

In one embodiment of the present invention, the charge carrier transport material, such as the diamine described hereinafter, may be incorporated into the photogenerating layer, or into the photoconductive layer in amounts, for example, ranging from about zero weight percent to 60 weight percent.

The charge carrier transport layers, such as layer 14, can be comprised of a number of suitable materials which are capable of transporting holes, this layer generally having a thickness in the range of from about 5 microns to about 50 microns, and preferably from about 10 microns to about 40 microns. In a preferred embodiment, this transport layer comprises molecules of the formula:

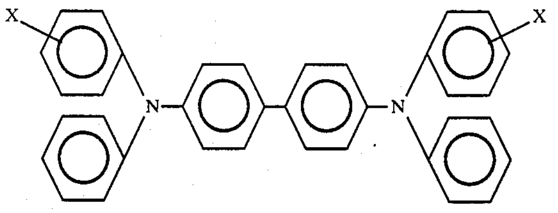

dispersed in a highly insulating and transparent organic resinous binder wherein X is selected from the group consisting of (ortho) $CH_3$, (meta) $CH_3$, (para) $CH_3$, (ortho) Cl, (meta) Cl, (para) Cl. The highly insulating resin, which has a resistivity of at least $10^{12}$ ohm-cm to prevent undue dark decay, is a material which is not necessarily capable of supporting the injection of holes. However, the insulating resin becomes electrically active when it contains from about 10 to 75 weight percent of the substituted N,N,N',N'-tetraphenyl[1,1-biphenyl]4-4'-diamines corresponding to the foregoing formula.

Compounds corresponding to the above formula include, for example, N,N'-diphenyl-N,N'-bis(alkylphenyl)-[1,1-biphenyl]-4,4'-diamine wherein the alkyl is selected from the group consisting of methyl such as 2-methyl, 3-methyl and 4-methyl, ethyl, propyl, butyl, hexyl and the like. With halo substitution, the amine is N,N'-diphenyl-N,N'-bis(halo phenyl)-[1,1'-biphenyl]-4,4'-diamine wherein halo is 2-chloro, 3-chloro or 4-chloro.

Other electrically active small molecules which can be dispersed in the electrically inactive resin to form a layer which will transport holes include, bis(4-diethylamino-2-methylphenyl)phenylmethane; 4',4''-bis(-diethylamino)-2',2''-dimethyltriphenylmethane; bis-4-(diethylaminophenyl)phenylmethane; and 4,4'-bis(diethylamino)-2,2'-dimethyltriphenylmethane.

Providing the objectives of the present invention are achieved, other charge carrier transport molecules can be selected for the photoconductive device of the present invention.

Examples of the highly insulating and transparent resinous material or inactive binder resinous material, for the transport layers include materials such as those described in U.S. Pat. No. 3,121,006 the disclosure of which is totally incorporated herein by reference. Specific examples of organic resinous materials include polycarbonates, acrylate polymers, vinyl polymers, cellulose polymers, polyesters, polysiloxanes, polyamides, polyurethanes and epoxies as well as block, random or alternating copolymers thereof. Preferred electrically inactive binder materials are polycarbonate resins having a molecular weight (Mw) of from about 20,000 to about 100,000 with a molecular weight in the range of from about 50,000 to about 100,000 being particularly preferred. Generally, the resinous binder contains from about 10 to about 75 percent by weight of the active material corresponding to the foregoing formula, and preferably from about 35 percent to about 50 percent of this material.

Also included within the scope of the present invention are methods of imaging with the photoresponsive devices illustrated herein. These methods of imaging generally involve the formation of an electrostatic latent image on the imaging member, followed by developing the image with known developer compositions, subsequently transferring the image to a suitable substrate and permanently affixing the image thereto. In those environments wherein the device is to be used in a printing mode, the imaging method involves the same steps with the exception that the exposure step is accomplished with a laser device, or image bar, rather than a broad spectrum white light source. In the later embodiment a photoresponsive device is selected that is sensitive to infrared illumination.

The invention will now be described in detail with reference to specific preferred embodiments thereof, it being understood that these examples are intended to be illustrative only. The invention is not intended to be limited to the materials, conditions, or process parameters recited herein, it being noted that all parts and percentages are by weight unless otherwise indicated.

EXAMPLE 1

In a 500 milliliter round-bottom flask there was placed 124.7 grams (1.12 moles) of m-fluoroaniline available from Aldrich Chemical, and 178.6 grams (1.68 mole) trimethyl orthoformate available from Aldrich Chemical. Thereafter 4.6 grams of concentrated sulfuric acid was added with mixing. The flask was then attached to a vacuum jacketed Vigreux distilling column (⅜" diameter×12" long), and the mixture was heated with stirring at an oil bath temperature of about 120° C. About 175 milliliters of methanol was distilled over in one hour. The bath temperature was then increased slowly to about 250° C., at which temperature it was maintained for 30 minutes. An additional amount about 25 milliliters of volatile materials was distilled over during this time.

Subsequently the reaction mixture was cooled to room temperature and the distillation apparatus was connected to a vacuum pump. The separated clear yellow liquid product N-methyl-m-fluoroformanilide, was isolated and purified by a vacuum distillation, affording 108.4 grams, about 63 percent. This product boils at about 78° C. at 0.19 mmHg.

EXAMPLE II

In a 1 liter flask, 108.4 grams (0.71 mole) of the N-methyl-m-fluoroformanilide as prepared in Example 1 was hydrolyzed with 350 milliliters of a 10 percent hydrochloric acid at refluxing temperature for 2 hours. The mixture was then cooled to room temperature, and rendered basic with a 15 percent potassium hydroxide solution. The organic layer that formed was then separated. The resulting aqueous layer was firstly saturated with potassium carbonate, and then extracted with ether (2×400 milliliters). The organic fractions were combined, washed with water and dried over magnesium sulfate anhydrous. After removing the ether by a rotary evaporator N-methyl-m-fluoroaniline, 76.5 grams, about 87 percent yield, a colorless liquid, was isolated, by reduced pressure distillation. This product boils at about 80° C. at 10 mmHg.

MS: mass spectrum 125 (M+).

Calculated for $C_7H_8NF$: C, 67.18; H, 6.44, N, 11.19, F, 15.18 Found: C, 67.24, H, 6.43, N, 11.32, F, 14.92.

EXAMPLE III

A mixture of N-methyl-m-fluoroanilide as prepared in Example II, 18.3 grams benzyl chloride, 0.14 mole available from Aldrich Chemical, 11.9 grams anhydrous sodium acetate, and 0.12 grams of iodine were heated at an oil bath temperature of about 110° C. for 12-16 hours.

The reaction mixture was then cooled to room temperature and transferred to a 250 milliliter separatory funnel with about 100 milliliters of water. The product solution was rendered basic with a sodium hydroxide solution, followed by extraction with ether (4×80 milliliters). The combined ether extract was washed with water, then dried over magnesium sulfate anhydrous. After removing the ether by a rotary evaporator, the product was isolated by vacuum distillation using a vacuum jacketed Vigreux distilling column. The product, N-methyl-N-benzyl-m-fluoroaniline, a colorless liquid, was isolated at 133°-138° C. at about 0.2 mmHg, yield 21.8 grams, about 90 percent.

MS: 215(M+).

Calculated for $C_{14}H_{14}NF$: C, 78.11, H, 6.56, N, 6.51, F, 8.83. Found: C, 78.14, H, 6.72, N, 6.54, F, 8.76.

EXAMPLE IV

N-methyl-N-p-chlorobenzyl-m-fluoroaniline was prepared from 17.5 grams (0.14 mole) of N-methyl-m-fluoroaniline, 23.7 grams (0.14 mole) p-chlorobenzyl chloride (Aldrich), 11.9 grams anhydrous sodium acetate and 0.12 grams iodine according to the procedure as described in Example III. Yield 25.8 grams (74 percent), boiling point 162°-170° C. at 0.13 mmHg.

MS: 249(M+).

Calculated for $C_{14}H_{13}NFCl$: C, 67.34; H, 5.25; N, 5.61; F, 7.61; Cl, 14.20. Found: C, 67.45; H, 5.22; N, 5.58; F, 7.47; Cl, 14.31.

EXAMPLE V

N-methyl-N-p-fluorobenzyl-m-fluoroaniline was prepared from 26.3 grams (0.21 mole) of N-methyl-m-fluoroaniline, 30.6 grams (0.21 mole) p-fluorobenzyl chloride (Aldrich), 17.8 grams anhydrous sodium acetate and 0.18 grams iodine according to the procedure described in Example III. Yield 35.4 grams (72 percent), boiling point 131°-137° C. at 0.2 mmHg.

MS: 233(M+).

Calculated for $C_{14}H_{13}NF_2$: C, 72.09; H, 5.62; N, 6.00; F, 16.29. Found: C, 72.00; H, 5.64; N, 5.92; F, 16.14.

EXAMPLE VI

N-methyl-N-m-chlorobenzyl-m-fluoroaniline was prepared from 17.5 grams (0.14 mole) of N-methyl-m-fluoroaniline, 23. grams (0.14 mole) m-chlorobenzyl chloride (Aldrich), 11.9 grams anhydrous sodium acetate and 0.12 grams iodine according to the procedure described in Example III. Yield 28.6 grams (83.7 percent), boiling point 172° C. at 0.07 mmHg.

MS: 249(M+).

Calculated for $C_{14}H_{13}NFCl$: C, 67.34, H, 5.25, N, 5.61, F, 7.61, Cl, 14.20. Found: C, 67.20, H, 5.39, N, 5.77, F, 7.70, Cl, 14.42.

EXAMPLE VII

Squaric acid, 1.14 grams (10 millimoles) and 4.31 grams (20 millimoles) of N-methyl-N-benzyl-m-fluoroaniline prepared in accordance with the process of Example III was heated to reflux in a mixture of toluene (40 ml) and 1 butanol (40 ml) at an oil bath temperature of about 130° C. Water was removed azeotropically by a Dean Stark trap. After 8 hours, the reaction mixture was cooled down to room temperature. The product, bis(2-fluoro-4-methylbenzylaminophenyl)squaraine was collected by filtration. After washing the product with ether and vacuum drying, 0.26 grams (4.7 percent) of green product pigment was obtained.

Melting Point: 239.5°-240.5° C.

Calculated for $C_{32}H_{26}N_2F_2O_2$: C, 75.58, H, 5.15, N, 5.51, F, 7.47. Found: C, 75.43, H, 5.10, N, 5.68, F, 7.38.

EXAMPLE VIII 1.14 grams (10 millimoles) of squaric acid and 4.31 grams (20 millimoles) of N-methyl-N-benzyl-m-fluoroaniline was allowed to react in 50 ml of 1-heptanol at an oil bath temperature of about 105° C. under a reduced pressure of about 70 mmHg. Water was distilled off azeotropically and collected by a Dean Stark trap. After 20 hours, the mixture was cooled to room temperature and filtered. After washing the pigment product with methanol and ether and vacuum drying, 1.48 grams (29.1 percent) of green pigment, bis(2-fluoro-4-methylbenzylaminophenyl)squaraine was obtained. This product was identified in accordance with the procedure of Example VII with substantially identical results.

EXAMPLE IX

The process of Example VII was repeated with the exception that there was selected 4.66 grams, about 20 millimoles of N-methyl-N-p-fluorobenzylaniline, as prepared in accordance with the procedure of Example IV in place of the N-methyl-N-benzyl-m-fluoroaniline, and there resulted 0.05 grams, 0.9 percent yield, of the pigment bis(2-fluoro-4-methyl-p-fluorobenzylaminophenyl)squarine.

Melting Point: 201.5°-202.5° C.

Calculated for $C_{32}H_{24}N_2F_4O_2$: C, 70.58, H, 4.44, N, 5.14, F, 13.96. Found: C, 70.60, H, 4.50, N, 5.03, F, 14.17.

EXAMPLE X

The process of Example VIII was repeated with the exception that there was selected 4.66 grams, 20 millimoles of N-methyl-N-p-fluorobenzylaniline, in place of the N-methyl-N-benzyl-m-fluoroaniline, and there resulted 1.57 grams, 28 percent yield, of the product bis(2-fluoro-4-methyl-p-fluorobenzylaminophenyl)squaraine. This product was identified in accordance with the procedure of Example IX, and substantially identical results were obtained.

EXAMPLE XI

The process as described in Example VIII was repeated with the exception that there was selected 4.98 grams, 20 millimoles of N-methyl-N-p-chlorobenzyl-m-fluoroaniline, in place of the N-methyl-N-benzyl-m-fluoroaniline, and there resulted 1.64 grams, 28.4 percent yield, bis(2-fluoro-4-methyl-p-chlorobenzylaminophenyl)squaraine.

Melting Point: 245.5°-247.0° C.

Calculated for $C_{32}H_{24}N_2O_2F_2Cl_2$: C, 66.56, H, 4.19, N, 4.85, F, 6.58, Cl, 12.28. Found: C, 66.50, H, 4.33, N, 4.76, F, 6.54, Cl, 12.27.

EXAMPLE XII

The process as described in Example VIII was repeated with the exception that there was selected 4.98 grams, 20 millimoles of N-methyl-N-m-chlorobenzyl-m-fluoroaniline, in place of N-methyl-N-benzyl-m-fluoroaniline, and there resulted 0.67 grams, 11.6 percent yield, of bis(2-fluoro-4-methyl-m-chlorobenzylaminophenyl)squaraine.

Melting Point: 220.6°-221.6° C.

Calculated for $C_{32}H_{24}N_2O_2F_2Cl_2$: C, 66.56, H, 4.19, N, 4.85, F, 6.58, Cl, 12.28. Found: C, 66.67, H, 4.30, N, 4.86, F, 6.72, Cl, 12.28.

EXAMPLE XIII

There was prepared a photoresponsive device containing as the photoconductive material the squaraine as prepared in accordance with Example VII, and as a charge transport layer an amine dispersed in a resinous binder. Specifically, there was prepared a photoresponsive device by providing a ball grained aluminum substrate, of a thickness of 150 microns, followed by applying thereto with a multiple clearance film applicator, in a wet thickness of 0.5 mils, a layer of N-methyl-3-aminopropyltrimethoxysilane, available from PCR Research Chemicals, Florida, in ethanol, in a 1:20 volume ratio. This layer was then allowed to dry for 5 minutes at room temperature, followed by curing for 10 minutes at 110° C. in a forced air oven.

A photoconductive layer containing 30 percent by weight of bis(2-fluoro-4-methylbenzylaminophenyl)-squaraine was then prepared as follows:

In separate 2 oz. amber bottles there was added 0.33 grams of the above squaraine, 0.75 grams of Vitel PE-200®, a polyester available from Goodyear, 85 grams of ⅛" stainless steel shot, and 20 ml of methylene chloride. The above mixtures were placed on a ball mill for 24 hours. The resulting slurry was then coated on the aluminum substrate with a multiple clearance film applicator, to a wet thickness of 1 mil. The layer was then allowed to air dry for 5 minutes. The resulting device was then dried at 135° C. for 6 minutes in a forced air oven. The dry thickness of the squaraine layer was about 1 micron.

The above photoconductive layer was then overcoated with a charge transport layer, which was prepared as follows:

A transport layer composed of 50 percent by weight Makrolon®, a polycarbonate resin available from Larbensabricken Bayer A.G., was mixed with 50 percent by weight N,N'-bis(3-methylphenyl)-1,1'-biphenyl-4,4'-diamine. This solution was mixed to 9 percent by weight in methylene chloride. All of these components were placed in an amber bottle and dissolved. The mixture was coated to give a layer with a dry thickness of 30 microns on top of the above squaraine photoconductive layer, using a multiple clearance film applicator (15 mils wet gap thickness). The resulting device was then air dried at room temperature for 20 minutes, followed by drying in a forced air oven at 135° C. for 6 minutes.

The above photoreceptor device was then incorporated into a xerographic imaging test fixture, and there resulted subsequent to development with toner particles containing a styrene n-butylmethacrylate resin, copies of excellent resolution and high quality.

EXAMPLE XIV

A photoreceptive device was prepared by providing an aluminized Mylar substrate in a thickness of 3 mils, and applying thereto a layer of 0.5 percent by weight of duPont 49,000 adhesive, a polyester available from duPont, in methylene chloride and 1,1,2-trichloroethane (4:1 volume ratio) with a Bird Applicator, to a wet thickness of 0.5 mils. The layer was allowed to dry for one minute at room temperature, and 10 minutes at 100° C. in a forced air oven. The resulting layer had a dry thickness of 0.5 microns.

A photogenerator layer containing 10 percent by weight of trigonal selenium, 25 percent by weight of N,N'-diphenyl-N,N'-bis(3-methylphenyl)1,1'-biphenyl-4,4'-diamine, and 65 weight percent of polyvinylcarbazole was then prepared as follows:

In a 2 oz. amber bottle was added 0.8 grams of polyvinylcarbazole and 14 milliliters, 1:1 volume ratio, tetrahydrofuran:toluene. There was then added to this solution 3.8 grams of trigonal selenium, and 100 grams ½" stainless steel shot. The above mixture was then placed on a ball mill for 72 to 96 hours. Subsequently, 5 grams of the resulting slurry were added to a solution of 0.18 grams of polyvinylcarbazole, and 0.15 grams of N,N'-diphenyl-N,N'-bis(3-methylphenyl)1,1'-biphenyl-4,4'-diamine, in 6.3 milliliters of tetrahydrofuran:toluene, volume ratio 1:1. This slurry was then placed on a shaker for 10 minutes. The resulting slurry was then coated on the above polyester interface with a Bird applicator, wet thickness of 0.5 mil and the resulting layer was then dried at 135° C. for 6 minutes in a forced air oven, resulting in a dry thickness of 2.0 microns.

A photoconductive layer containing 30 percent by weight of bis(2-fluoro-4-methylbenzylaminophenyl)-squaraine was then prepared by repeating the procedure of Example XIII, which layer dry thickness 1 micron was coated on the above photogenerator layer with a Bird applicator.

The above photoconductive layer was then overcoated with a charge transport layer which was prepared as follows:

A transport layer comprised of 50 percent by weight Markrolon®, a polycarbonate resin available from Larbensabricken Bayer A.G, was mixed with 50 percent by weight N,N'-bis(3-methylphenyl)-1,1'-biphenyl-4,4'-diamine. This solution was mixed to 9 percent by weight of methylene oxide. All of these components were placed into an amber bottle and dissolved. Subsequently, the resulting mixture was coated to give a layer with a dry thickness of 30 microns on top of the above photoconductive squaraine layer, which coating was accomplished with a multiple clearance film applicator, 15 mils wet gap thickness. The resulting device was then dried in air at room temperature for 20 minutes and then in a forced air oven at 135° C. for 6 minutes.

There resulted a photoresponsive device containing an aluminized Mylar supporting substrate, a photogenerating layer of trigonal selenium, a photoconductive layer of bis(2-fluoro-4-methylbenzylaminophenyl)-squaraine and as a top layer a charge transport layer of the amine indicated.

Other photoresponsive devices are also prepared by repeating the procedure of Example XIII, and Example XIV with the exception that there was selected as the photogenerating layer a selenium tellurium alloy, containing 75 percent by weight of selenium and 25 percent by weight of tellurium, or an arsenic selenium alloy, containing 99.99 percent by weight of selenium and 0.1 percent by weight of arsenic.

Further, photoresponsive devices were prepared by repeating the procedure of Examples XIII and XIV with the exception that there was selected as the squaraine photoconductive composition bis(2-fluoro-4-methyl-p-chlorobenzylaminophenyl)squaraine, bis(2-fluoro-4-methyl-p-fluorobenzylaminophenyl)squaraine, and bis(2-fluoro-4-methyl-m-chlorobenzylaminophenyl)squaraine.

The devices as prepared in Examples XIII and XIV were then tested for photosensitivity in the visible infrared region of the spectrum by negatively charging the devices with corona to −800 volts, followed by simultaneously exposing each device to monochromic light in the wavelength region of about 400 to about 1,000 manometers. The photoresponsive device of Example XIII responded to light in the wavelength region of 400 to 950 manometers, indicating visible and infrared photosensitivity, and the device of Example XIV had excellent response in the wavelength region of from about 400 to about 950 nanometers, indicating both visible and infrared photosensitivity for this device.

Moreover, the photoresponsive device as prepared in accordance with Example XIV was incorporated into a xerographic imaging test fixture and there results subsequent to development with toner particles containing a styrene n-butylmethacrylate resin, copies of excellent resolution and high quality.

Although the invention has been described with reference to specific preferred embodiments, it is not intended to be limited thereto, rather those skilled in the art will recognize variations and modifications may be made therein which are within the spirit of the present invention and within the scope of the following claims.

We claim:

1. Squaraine compositions selected from the group consisting of bis(2-fluoro-4-methylbenzylaminophenyl)-squaraine, bis(2-fluoro-4-methyl-p-chlorobenzylaminophenyl)squaraine, bis(2-fluoro-4-methyl-p-fluorobenzylaminophenyl)squaraine, and bis(2-fluoro-4-methyl-m-chlorobenzylaminophenyl)squaraine.

2. The squaraine composition bis(2-fluoro-4-methylbenzylaminophenylene)squaraine.

3. The squaraine composition bis(2-fluoro-4-methyl-p-chlorobenzylaminophenyl)squaraine.

4. The squaraine composition bis(2-fluoro-4-methyl-p-fluorobenzylaminophenyl)squaraine.

5. The squaraine composition bis(2-fluoro-4-methyl-m-chlorobenzylaminophenyl)squaraine.

* * * * *